United States Patent
Cirera Santasusana et al.

(10) Patent No.: US 9,174,378 B2
(45) Date of Patent: Nov. 3, 2015

(54) COSMETIC TEXTILE FIBER, METHOD FOR OBTAINING IT AND USE THEREOF

(75) Inventors: Alfonso Cirera Santasusana, Blanes (ES); Esteve Soy Fabra, Blanes (ES)

(73) Assignee: NYLSTAR, S.A. (ES)

( * ) Notice: Subject to any disclaimer, the term of this patent is extended or adjusted under 35 U.S.C. 154(b) by 0 days.

(21) Appl. No.: 13/816,833

(22) PCT Filed: Jul. 28, 2011

(86) PCT No.: PCT/EP2011/062974
§ 371 (c)(1),
(2), (4) Date: Jul. 26, 2013

(87) PCT Pub. No.: WO2012/022597
PCT Pub. Date: Feb. 23, 2012

(65) Prior Publication Data
US 2013/0302386 A1 Nov. 14, 2013

(30) Foreign Application Priority Data

Aug. 16, 2010 (ES) .................................. 201031260

(51) Int. Cl.
| | | |
|---|---|---|
| B29C 47/06 | (2006.01) | |
| A61Q 19/00 | (2006.01) | |
| D01F 1/10 | (2006.01) | |
| D01F 6/60 | (2006.01) | |
| A61K 8/73 | (2006.01) | |
| A61K 8/88 | (2006.01) | |
| A61K 8/19 | (2006.01) | |
| A61K 8/34 | (2006.01) | |
| B29D 99/00 | (2010.01) | |
| A61K 9/70 | (2006.01) | |
| A61K 33/24 | (2006.01) | |
| A61K 47/48 | (2006.01) | |
| B29K 77/00 | (2006.01) | |
| B29K 105/16 | (2006.01) | |
| B29K 505/14 | (2006.01) | |
| B29L 31/00 | (2006.01) | |

(52) U.S. Cl.
CPC . *B29C 47/06* (2013.01); *A61K 8/19* (2013.01); *A61K 8/34* (2013.01); *A61K 8/735* (2013.01); *A61K 8/88* (2013.01); *A61K 9/70* (2013.01); *A61K 33/24* (2013.01); *A61K 47/4823* (2013.01); *A61Q 19/00* (2013.01); *B29D 99/0078* (2013.01); *D01F 1/10* (2013.01); *D01F 6/60* (2013.01); *A61K 2800/413* (2013.01); *A61K 2800/57* (2013.01); *A61K 2800/594* (2013.01); *B29K 2077/00* (2013.01); *B29K 2105/162* (2013.01); *B29K 2471/02* (2013.01); *B29K 2489/00* (2013.01); *B29K 2505/14* (2013.01); *B29L 2031/731* (2013.01)

(58) Field of Classification Search
CPC ... A61K 2800/413; A61K 8/735; A61K 8/88; A61Q 19/00; D01F 6/60
See application file for complete search history.

(56) References Cited

U.S. PATENT DOCUMENTS

| | | | | |
|---|---|---|---|---|
| 3,949,741 | A * | 4/1976 | Hofmann | 606/204.35 |
| 6,620,927 | B2 | 9/2003 | Bulpitt | |
| 2009/0124188 | A1 | 5/2009 | Levy | |
| 2011/0059143 | A1* | 3/2011 | Iavarone et al. | 424/401 |

FOREIGN PATENT DOCUMENTS

| | | |
|---|---|---|
| DE | 102008030111 A | 12/2009 |
| EP | 1482252 A2 | 12/2004 |
| EP | 2228393 A1 * | 9/2010 |
| ES | 2326721 A1 * | 10/2009 |
| JP | 2001227772 A | 8/2001 |
| WO | 9010020 A | 9/1990 |
| WO | 2009087254 A | 7/2009 |
| WO | 2009156058 A1 | 12/2009 |

OTHER PUBLICATIONS

Lee, H.; Lee, K.; Kim, I.K.; Park, T.G. "Synthesis, characterization, and in vivo diagnostic applications of hyaluronic acid immobilized gold nanoprobes" Biomaterials 29 (2008) 4709-4718.*

Cheng H. et al., Polyethylene glycol-stabilized platinum nanoparticles: The efficient and recyclable catalysts for selective hydrogenation of o-chloronitrobenzene to o-chloroaniline, Journal of Colloid and Interface Science, Academic Press, New York, NY, 2009, vol. 336, pp. 675-678.

Lee H. et al., Direct visualization of hyaluronic acid polymer chain by self-assembled one-dimensional array of gold nanoparticles, Macromolecules, American Chemical Society, 2006, vol. 39, pp. 23-25.

European Search Report, PCT Application No. PCT/EP2011/062974 dated Nov. 24, 2011.

Lee H. et al., Synthesis, characterization, and in vivo diagnostic applications of hyaluronic acid immobilized gold nanoprobes, BioMaterials, Elsevier Science Publishers BV., Barking, GB, 2008, vol. 29, No. 35, pp. 4709-4718.

European Search Report, Application No. EP11382175, dated Nov. 2, 2011.

European Search Report, PCT Application No. PCT/ES2009/00001, dated May 28, 2009.

* cited by examiner

*Primary Examiner* — Brian-Yong Kwon
*Assistant Examiner* — Andrew S Rosenthal
(74) *Attorney, Agent, or Firm* — Kramer Levin Naftalis & Frankel LLP

(57) ABSTRACT

The present invention describes a polyamide textile fiber comprising conjugated nanoparticles homogeneously dispersed in the fiber, selected from polyethylene glycol-conjugated platinum nanoparticles, hyaluronic acid-conjugated gold nanoparticles and mixtures thereof. The invention also describes how to obtain it as well as its use in a cosmetic skin treatment as a system for the release of said conjugated nanoparticles.

19 Claims, 3 Drawing Sheets

COSMETIC TEXTILE FIBER, METHOD FOR OBTAINING IT AND USE THEREOF

CROSS REFERENCE TO RELATED APPLICATIONS

This application is the U.S. national phase filing of the corresponding international application No. PCT/EP2011/062974 filed on Jul. 28, 2011, and published as WO 2012/022597 A1, which application is hereby incorporated herein by reference in its entirety.

FIELD OF THE INVENTION

The present invention relates to a textile product, particularly to a new polyamide-based textile fiber comprising nanoparticles homogeneously distributed over the entire fiber, as well as a method for obtaining it. Said textile fiber is useful for manufacturing various textile products and has cosmetic properties.

BACKGROUND OF THE INVENTION

Different textile products incorporating cosmetic active ingredients capable of conferring hydrating, antioxidant or firming properties thereto are known in the state of the art. In all the cases, it has been seen that the active ingredient is added to the fiber once the latter has been manufactured, such that said active ingredient is only bound to the surface of the fiber and is thus gradually released in the skin.

However, fibers of this type have various drawbacks among which the low effectiveness and durability of the cosmetic effect provided by them can be mentioned.

There is therefore a need in the state of the art to provide a new textile fiber with cosmetic properties which at least partially overcomes any of these drawbacks.

DESCRIPTION OF THE INVENTION

Figure 1:
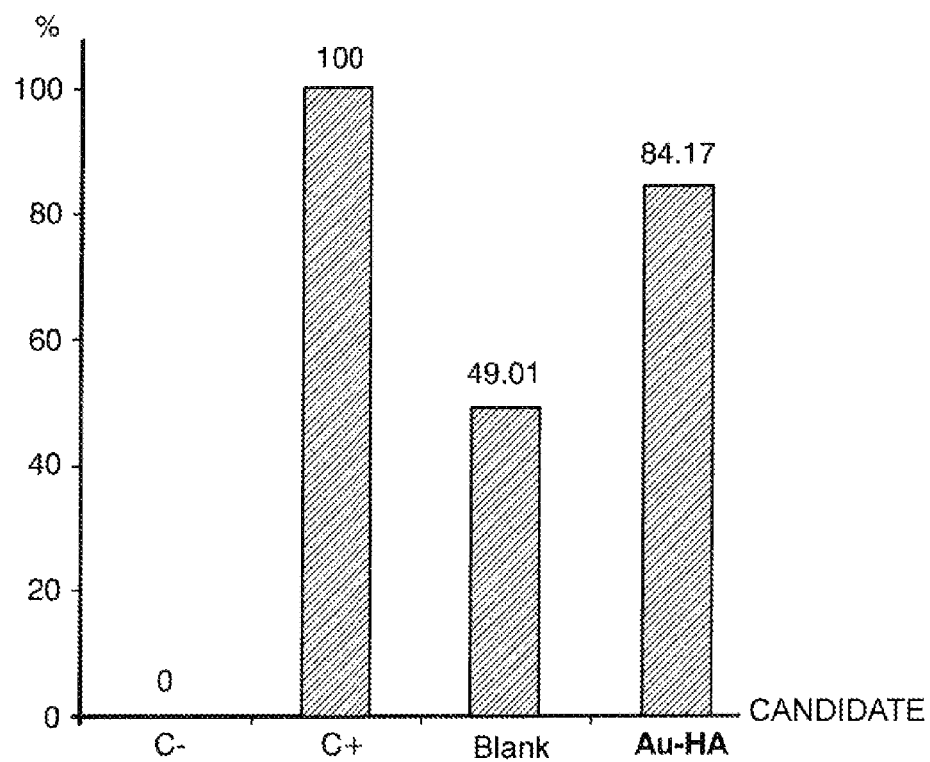
FIG. 1 shows an increase of the antioxidant effect (normalized to % with respect to the positive control, 100%) of the textile fiber with Au-HA (Au-HA) compared with the effect of fibers without Au-HA (Blank) and a positive control (C+: Ascorbic acid) and negative control (C−: Base medium).

In one aspect, the invention relates to a method for obtaining a textile fiber comprising conjugated nanoparticles homogeneously distributed over the entire fiber which confer cosmetic properties thereto.

The conjugated nanoparticles useful for putting the present invention into practice are hyaluronic acid-conjugated gold nanoparticles, polyethylene glycol (PEG)-conjugated platinum nanoparticles and mixtures thereof. Conjugated nanoparticles of this type used in the present invention withstand these high temperatures of the method for obtaining textile fibers without degrading.

In a particular embodiment, the textile fiber of the invention comprises hyaluronic acid-conjugated gold nanoparticles. The hyaluronic acid-conjugated gold nanoparticles useful for putting the present invention into practice are described in patent application WO2009087254, the content of which is incorporated herein by reference.

In a preferred embodiment of the present invention, the conjugated gold nanoparticles have an average size comprised between 4 and 50 nm, more preferably of 10 nm. Their concentration in the textile fiber strongly depends on the size. For the case of the 10 nm nanoparticles, it is $6*10E12$ np/ml. In a particular embodiment, the concentration of conjugated gold nanoparticles in the fiber is 15 ppm on average.

The hyaluronic acid oligomers preferably used for being conjugated to the gold of the nanoparticles have an average molecular weight of 5 KDa.

In another particular embodiment, the textile fiber of the invention comprises polyethylene glycol (PEG)-conjugated platinum nanoparticles. In this case, and as in the case of the gold and hyaluronic acid nanoparticles, the PEG is bound to the Pt of the nanoparticle by derivatizing it with a cystamine containing an SH group, since Pt, like Au, has a high chemical affinity for this group and a covalent bond between the metal of the nanoparticle and the SH is produced.

The textile fiber, hereinafter textile fiber of the invention, is a polyamide, preferably polyamide 66, fiber. The shape of its cross-section is not particularly limiting, being able to be, among others, circular, triangular, hollow, flattened or star-shaped. The type of fiber can be of different types, from the finest ones of 8 g/1000 m of strand to the thickest ones of 1000 g/1000 m.

The fiber of the invention can optionally further comprise additives such as flame retardants, deodorizers, mothproofing agents, UV absorbers, and the like in amounts which do not compromise the cosmetic safety and efficacy thereof.

In a particular embodiment the fiber of the invention contains more than of $4\times10^9$ conjugated per square centimeter. The conjugated nanoparticles are homogeneously incorporated over the entire textile fiber.

The fiber of the invention can in principle be obtained by means of any conventional method such as the one described below which is an additional aspect of the present invention.

The method, hereinafter method of the invention, comprises the following steps of:
(i) preparing a masterbatch from a part of the total amount of starting polyamide of the method and the conjugated nanoparticles;
(ii) diluting the masterbatch obtained in (i) with the rest of the polyamide;
(iii) heating the resulting mass until obtaining a fluid and homogeneous mass; and
(iv) shaping the mass obtained in the previous step in the form of strands.

The preparation of the masterbatch is performed in a conventional manner. It comprises mixing a part of all the starting polyamide which is used in the method and which is in the form of solid pellets with an amount of conjugated nanoparticles. If one or more conventional additives are to be incorporated to the fiber, they can also be added in this step of obtaining the masterbatch. The mixture is melted, shaped and cooled, giving rise to solid pellets comprising a high concentration of homogeneously distributed conjugated nanoparticles.

The proportions between the amount of masterbatch and the rest of the polyamide used in step (ii) are adjusted such that the desired concentration of conjugated in the resulting textile fiber is reached.

The mixture resulting from step (ii) is heated to a temperature typically comprised between 200-300° C. The resulting molten and homogeneous mass is passed through conduits conferring the form of a strand thereto. Finally, the strands are cooled, giving rise to the textile fiber of the invention.

In the method of the invention, the loading module allows the feeding, in a continuous and automatic manner, of the feeding system for feeding product into the molten mass of the extruder. The filling of product into the loading system is performed manually. From this point the system works automatically. Since the polyamide 66 (PA6.6) base material is oxidized and degraded in the presence of temperatures and oxygen, the entire system must be pressurized in an inert atmosphere of nitrogen at 50 mbar. The feeding system must be provided with tight valves, balancing valves and nitrogen purge valves. After any loading of product, a nitrogen sweep must be performed before connecting the tank to the process. For this section, it is necessary to construct and subsequently install a receiver tank for the additives as well as the necessary auxiliary elements, valves, sensors, etc. For a higher efficiency of the system, work is done at outlet pressures of 130 bar and a final temperature of 298° C. In a particular embodiment, $4 \times 10^9$ Au-HA nanoparticles per square centimeter of PA6.6 are loaded in a first masterbatch.

The fibers of the present invention have cosmetic properties. As has been mentioned above, the conjugated nanoparticles are homogeneously incorporated over the entire textile fiber so they have a high effectiveness and durability of the cosmetic effect and provide an ease of use.

When the textile fiber of the invention comes into contact with the skin, the conjugated nanoparticles leave the fiber and are administered to the skin. The textile fiber is therefore is a cosmetic system for the topical release of conjugated nanoparticles to the skin.

In this sense, when the textile fiber is used to manufacture a garment, the consumer must only wear it for the cosmetic treatment provided by the textile fiber or the textile product manufactured from the textile fiber of the invention, which is another aspect of the present invention, to take place. Therefore, both the textile fiber of the invention as well as a textile product derived therefrom are a topical system for the administration of conjugated nanoparticles providing a cosmetic effect to the consumer.

The textile fiber of the invention with Au-HA nanoparticles (of Example 1) distributed over the entire fiber and its cosmetic effects have been analyzed by the inventors as is set forth below. In one aspect, this fiber has an antioxidant effect since the hyaluronic acid-conjugated gold nanoparticles protect the skin against the free radicals present in the atmosphere which are responsible for skin aging. When the conjugates contact the free radicals, they neutralize their capacity to damage the skin. This effect has been proved with the DPPH technique, the most accepted technique in cosmetics to evaluate the antioxidant effect with this textile fiber with Au-HA nanoparticles.

The results obtained show an increase of the antioxidant effect of the textile fiber with Au-HA nanoparticles compared with the effect of fibers without Au-HA nanoparticles. The antioxidant levels of the textile fiber with Au-HA nanoparticles are even close to the positive control used in the experiment (C+: ascorbic acid) (see FIG. 1).

The release of Au-HA nanoparticles from the fiber has been evaluated using the ICP-M technique (Metal Analysis Unit, University of Barcelona) and has demonstrated that 0.6% of the Au-HA nanoparticles are released to the skin every 48 hours.

Figure 2:
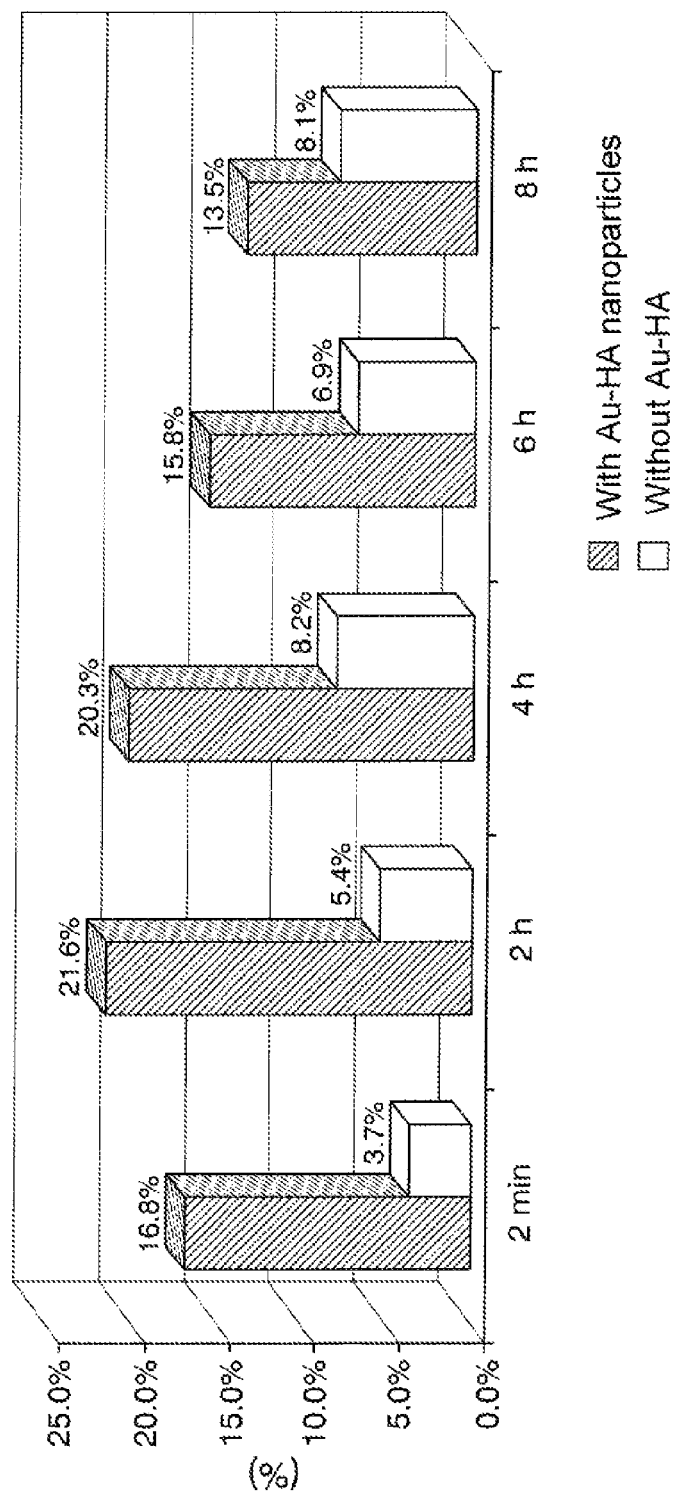
FIG. 2 is a comparative corneometry (skin hydration analysis) assay in the case of a forearm treated with a solution with 3% of Au-HA nanoparticles and a solution without Au-HA nanoparticles.

When the Au-HA nanoparticles are in contact with the skin, the hyaluronic acid layer of the nanoparticles causes a deep hydration due to the capacity of hyaluronic acid to absorb and retain water in its structure. In vivo efficacy assays have been carried out with volunteers on the skin of the forearm (SpinControl, France) to evaluate this hydrating effect. The study demonstrates that the Au-HA nanoparticles have an intense hydrating effect on the surface of the skin (see FIG. 2). In all the cases, it is seen how the variation of the corneometer parameter (percentage of skin hydration) is greater in the case of the forearm treated with fiber containing Au-HA nanoparticles (variations of 16.8%, 21.6%, 20.3%, 15.8% and 13.5% versus smaller variations of 3.7%, 5.4%, 8.2%, 6.9% and 8.1% respectively) with fibers without Au-HA.

The textile fiber with Au-HA nanoparticles has also proved to have an anti-aging cosmetic effect. The cells of the skin produce endogenous HA which plays a decisive role in maintaining the skin young and healthy. As age increases, the amount of HA in the skin decreases since the cells progressively lose their capacity to produce it. The Au-HA nanoparticles act directly on the cells of the skin, providing an anti-aging effect at genetic level which increases the capacity of the cells to produce HA. Due to this effect the skin recovers its youth and elasticity.

Figure 3:
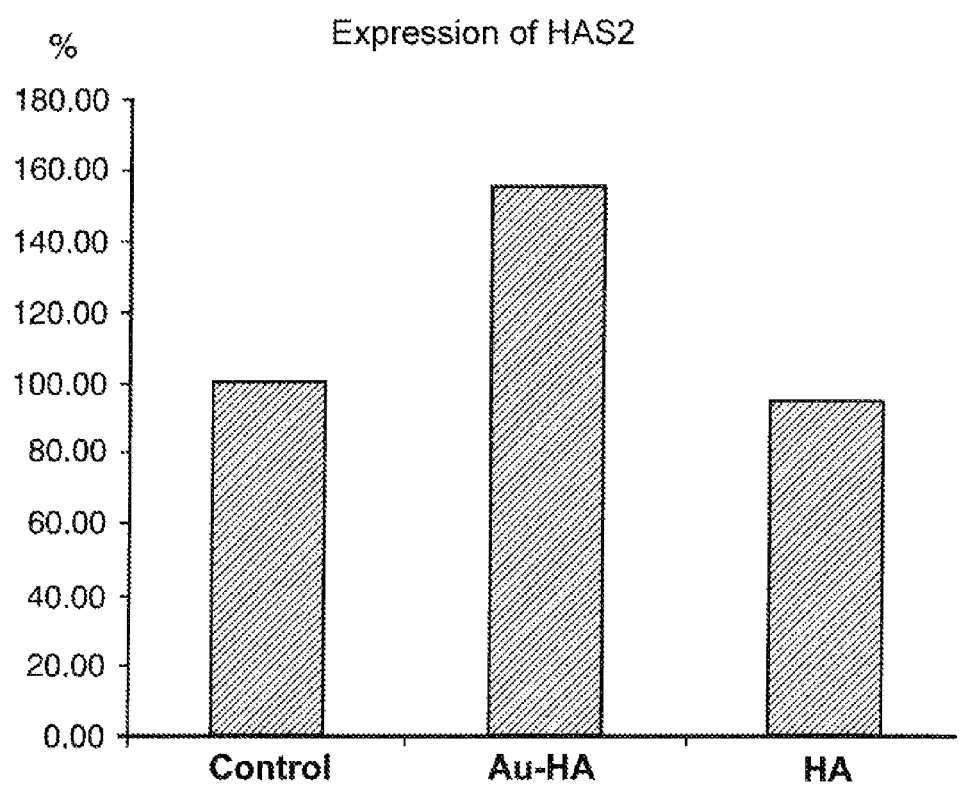
FIG. 3: represents a comparative assay showing that the cells treated with 3% Au-HA nanoparticles increase by 60% the expression of the HAS2 gene compared with untreated cells (Control) and cells treated with HA without conjugation to gold nanoparticles.

This effect has been demonstrated by the inventors through the evaluation of the expression levels of RNA of the HAS2 gene (hyaluronic acid synthase 2) (responsible for the production of natural HA). It has been verified that the cells treated with Au-HA nanoparticles increase by 60% the production of HAS2 compared with untreated skin (Control) and with a treatment using isolated HA (see FIG. 3).

The safety of the Au-HA nanoparticles has been evaluated in clinical trials (Evic Hispania, Barcelona) with volunteers, the highest qualifications in terms of dermatological compatibility being obtained.

Therefore, in another aspect the invention relates to the use of the textile fiber of the invention as well as of a textile product manufactured therefrom for its use in a cosmetic treatment.

Illustrative examples of the invention are presented below, which are set forth for a better understanding of the invention and in no case must they be considered as a limitation of the scope thereof.

EXAMPLES

Example 1

Obtaining a Textile Fiber According to the Invention with Au-HA Nanoparticles (NylGold®)

1.1: Synthesis of Gold Nanoparticles

An aqueous solution (150 mL) of sodium citrate (2.2 mM) was heated to boiling with vigorous stirring. Then, 1 mL of an aqueous solution (23.4 mM) of $HAuCl_4$ was added to the solution at boiling. The reduction took place in approximately 2 minutes and a solution of gold nanoparticles was formed, which experienced an indicative change in color from purplish to intense red. Finally, the reactor was separated from the heat source and left to cool to room temperature. The gold nanoparticles thus obtained were characterized by means of UV-Vis (521.2 nm). The absorption spectra were recorded with a Shimadzu UV-240IPC spectroscope.

1.2: Functionalization of Gold (Au) Nanoparticles with 5 KDa Derivatized HA. Derivatization of the 5 KDa HA Oligomers To thiolate 1 gram of 5 KDa HA, 3.9 g of cystamine hydrochloride were added in 200 ml of a buffer which was prepared from 3.09 g of $H_3BO_3$ and 11.7 g of NaCl in 500 ml of water, the pH was adjusted to 8.5 with 1M NaOH.

The solution was placed at 45° C., 2.5 g of sodium cyanoborohydride were added. The reaction was performed under argon and left for 4-5 days. 1.8 g of dithiothreitol were added, the reaction was stopped an hour later.

Once thiolated, a dialysis was performed to extract the excess of DTT and of cystamine. The membranes were of 3.5 KDa and the dialysis buffer consisted of 5 L of water with 3 g of NaCl and 1.5 ml 1M HCl twice in one day. The next two days, four changes of 5 L of water with 1.5 ml of 1M HCl were made.

Conjugation of Gold Nanoparticles to Derivatized 5 KDa HA

The gold nanoparticles obtained in Example 1.1 were conjugated with the derivatized 5 KDa oligomers obtained, by means of adding 0.5 mg in 1 mL of solution of nanoparticles. The reaction was carried out at room temperature and with magnetic stirring for 30 minutes. The reaction was stopped by decreasing the temperature (inside the refrigerator). The purification was performed by dialysis (10 KDa MWCO) against sodium citrate (2.3 mM, 3.25 g/5 L $H_2O$). To obtain the dry product, the Au-HA product was frozen and lyophilized.

The invention claimed is:

1. A topical system comprising polyamide textile fiber comprising conjugated nanoparticles selected from polyethylene glycol-conjugated platinum nanoparticles, hyaluronic acid-conjugated gold nanoparticles and mixtures thereof, wherein the conjugated nanoparticles are homogeneously incorporated over the entire textile fiber for high effectiveness and durability of the cosmetic effect, and said topical system is intended for a homogenous release of conjugated nanoparticles to the skin.

2. The fiber of claim 1, wherein the polyamide is polyamide 66.

3. The fiber of claim 1, wherein the nanoparticles are hyaluronic acid-conjugated gold nanoparticles.

4. The fiber of claim 3, wherein the gold nanoparticles have a size of 10 nm and the conjugated hyaluronic acid has an average molecular weight of 5 KDa.

5. The fiber of claim 1, wherein the nanoparticles are polyethylene glycol-conjugated platinum nanoparticles.

6. A method for preparing the textile fiber claim 1, comprising:
(i) preparing a masterbatch from a part of the total amount of starting polyamide and the conjugated nanoparticles;
(ii) diluting the masterbatch with the rest of the polyamide;
(iii) heating the resulting mass until obtaining a fluid and homogeneous mass; and
(iv) shaping the homogenous mass into strands.

7. The topical system of claim 1, wherein the textile fiber is used at least one of (i) for the preparation of a textile product, (ii) in a cosmetic treatment, and (iii) as a system for the release of hyaluronic acid-conjugated gold nanoparticles and/or of polyethylene glycol-conjugated platinum nanoparticles.

8. The topical system of claim 1, wherein a textile product manufactured from said fiber is used at least one of (i) in a cosmetic treatment, and (ii) as a system for the release of hyaluronic acid-conjugated gold nanoparticles and/or of polyethylene glycol-conjugated platinum nanoparticles.

9. A method for preparing the textile fiber of claim 2, comprising:
(i) preparing a masterbatch from a part of the total amount of starting polyamide and the conjugated nanoparticles;
(ii) diluting the masterbatch with the rest of the polyamide;
(iii) heating the resulting mass until obtaining a fluid and homogeneous mass; and
(iv) shaping the homogenous mass into strands.

10. A method for preparing the textile fiber of claim 3, comprising:
(i) preparing a masterbatch from a part of the total amount of starting polyamide and the conjugated nanoparticles;
(ii) diluting the masterbatch with the rest of the polyamide;
(iii) heating the resulting mass until obtaining a fluid and homogeneous mass; and
(iv) shaping the homogenous mass into strands.

11. A method for preparing the textile fiber of claim 4, comprising:
(i) preparing a masterbatch from a part of the total amount of starting polyamide and the conjugated nanoparticles;
(ii) diluting the masterbatch with the rest of the polyamide;
(iii) heating the resulting mass until obtaining a fluid and homogeneous mass; and
(iv) shaping the homogenous mass into strands.

12. A method for preparing the textile fiber of claim 5, comprising:
(i) preparing a masterbatch from a part of the total amount of starting polyamide and the conjugated nanoparticles;
(ii) diluting the masterbatch with the rest of the polyamide;
(iii) heating the resulting mass until obtaining a fluid and homogeneous mass; and
(iv) shaping the homogenous mass into strands.

13. The fiber of claim 2, wherein the nanoparticles are hyaluronic acid-conjugated gold nanoparticles.

14. The fiber of claim 13, wherein the gold nanoparticles have a size of 10 nm and the conjugated hyaluronic acid has an average molecular weight of 5 KDa.

15. The fiber of claim 2, wherein the nanoparticles are polyethylene glycol-conjugated platinum nanoparticles.

16. The fiber of claim 2, wherein a textile product manufactured from said fiber is used at least one of (i) in a cosmetic treatment, and (ii) as a system for the release of hyaluronic acid-conjugated gold nanoparticles and/or of polyethylene glycol-conjugated platinum nanoparticles.

17. The fiber of claim 3, wherein a textile product manufactured from said fiber is used at least one of (i) in a cosmetic treatment, and (ii) as a system for the release of hyaluronic acid-conjugated gold nanoparticles and/or of polyethylene glycol-conjugated platinum nanoparticles.

18. The fiber of claim 4, wherein a textile product manufactured from said fiber is used at least one of (i) in a cosmetic treatment, and (ii) as a system for the release of hyaluronic acid-conjugated gold nanoparticles and/or of polyethylene glycol-conjugated platinum nanoparticles.

19. The fiber of claim 5, wherein a textile product manufactured from said fiber is used at least one of (i) in a cosmetic treatment, and (ii) as a system for the release of hyaluronic acid-conjugated gold nanoparticles and/or of polyethylene glycol-conjugated platinum nanoparticles.

* * * * *